United States Patent [19]

Immel et al.

[11] 4,137,263

[45] Jan. 30, 1979

[54] PROCESS FOR THE EVAPORATION OF CYCLOHEXANONE OXIME

[75] Inventors: Otto Immel; Bernd-Ulrich Kaiser; Hans-Helmut Schwarz; Klaus Starke, all of Krefeld, Germany

[73] Assignee: Bayer Aktiengesellschaft, Germany

[21] Appl. No.: 831,790

[22] Filed: Sep. 9, 1977

[30] Foreign Application Priority Data

Sep. 15, 1976 [DE] Fed. Rep. of Germany ....... 2641414

[51] Int. Cl.$^2$ ............................................. C07C 131/04

[52] U.S. Cl. ................................................. 260/566 A

[58] Field of Search .................................... 260/566 A

[56] References Cited

FOREIGN PATENT DOCUMENTS 999851 7/1965 United Kingdom ................ 260/566 A

*Primary Examiner*—Gerald A. Schwartz

*Attorney, Agent, or Firm*—Connolly and Hutz

[57] ABSTRACT

A process for the evaporation of cyclohexanone oxime, wherein the cyclohexanone oxime is evaporated in the presence of an inert gas at a superatmospheric pressure of at least 300 Torr at 110° to 160° C, the evaporation temperature being governed by the inert gas pressure or by the ratio of cyclohexanone oxime to inert gas.

3 Claims, 1 Drawing Figure

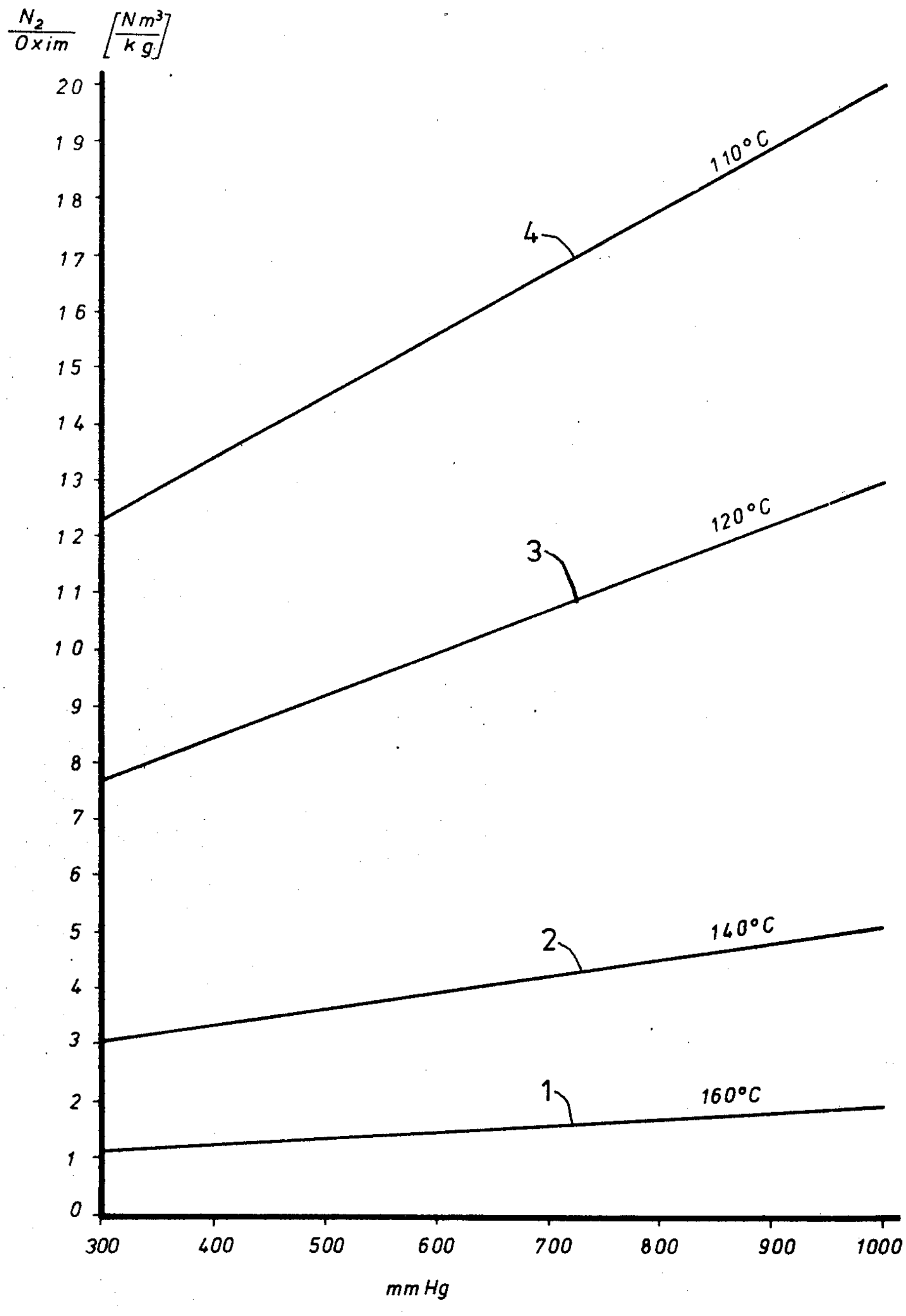
N2 / Oxim [Nm3 / kg]
20
19
18
17
16
15
14
13
12
11
10
9
8
7
6
5
4
3
2
1
0
110°C
120°C
140°C
160°C
4
3
2
1
300
400
500
600
700
800
900
1000
mm Hg

PROCESS FOR THE EVAPORATION OF CYCLOHEXANONE OXIME

ε-caprolactam can be produced from cyclohexanone oxime be rearranging the cyclohexanone oxime in the gas phase on solid catalysts, for example, boron oxide catalysts. The cyclohexanone oxime has to be in vapour form for this process. Unfortunately, it is impossible to evaporate cyclohexanone oxime without partial decomposition. The cyclohexanone oxime vapour usually contains decomposition products in a quantity impairing the quality of the ε-caprolactam formed and, additionally, crusts are formed in the evaporators.

The present invention provides a process for the evaporation of cyclohexanone oxime, wherein the cyclohexanone oxime is evaporated in the presence of an inert gas at a superatmospheric pressure of at least 300 Torr and at 110° to 160° C., preferably 120° to 140° C., the evaporation temperature being governed by the inert gas pressure or by the weight ratio of cyclohexanone oxime to inert gas.

If these conditions are observed, the cyclohexanone oxime is evaporated almost completely, no crusts are formed in the evaporator and virtually no decomposition occurs. The indicated conditions are critical as cyclohexanone oxime decomposes at a superatmospheric pressure of less than 300 Torr, crusts are formed at temperatures below 110° C. and decomposition and marked discoloration occur at temperatures above 160° C.

Nitrogen is preferably used as the inert gas. For evaporation, water can be added to the cyclohexanone oxime in amounts of up to 10% by weight, based on the oxime, and forced-circulation falling-film evaporators or similar apparatus are preferably used for evaporation.

The accompanying drawing (FIG. 1) shows a graph from which the preferred conditions for the process can be read off. The superatmospheric pressure in Torr (= mm Hg) is recorded on the abscissa and the ratio of the quantity of inert gas (nitrogen) in normal cubic meters ($Nm^3$) to the quantity of cyclohexanone oxime in kilograms is recorded on the ordinate. The lines 1 to 4 shown in the graph represent the evaporation temperatures. Line 1 corresponds to a temperature of 160° C., line 2 to a temperature of 140° C., line 3 to a temperature of 120° C., and line 4 to a temperature of 110° C. The operating range of the process is situated between lines 1 and 4; the preferred range between lines 2 and 3. The graph shows the necessary quantity of inert gas per unit weight of cyclohexanone oxime for any given superatmospheric pressure and temperature.

EXAMPLE 200 kg/h of cyclohexanone oxime with a water content of 7.6% by weight were introduced into a falling-film evaporator. The evaporator had forced circulation and a total of about 2000 kg/hour were circulated. $6m^3$ of nitrogen per kg of cyclohexanone oxime were passed through the falling-film evaporator. The excess pressure was 450 mm Hg and the temperature in the sump of the evaporator was 130° C.

The evaporated cyclohexanone oxime was rearranged in the gas phase on a boric acid catalyst to form caprolactam. 1.5 kg/h of cyclohexanone oxime were removed from the forced circuit of the falling-film evaporator. The test was conducted continously over a period of several weeks without any crusts being formed in the evaporator.

Comparison

1. The procedure was as in Example 1, except that 18 $m^3$ of nitrogen were introduced per kg of cyclohexanone oxime. The excess pressure was 450 mm Hg, although the temperature was only 105° C. The apparatus became encrusted after only a few days.

2. The procedure was as in Example 1, except that only 1 $m^3$ of nitrogen were added per kg of cyclohexanone oxime. The temperature rose to 165° C., heavy discoloration occured in the cyclohexanone oxime evaporated, the caprolactam obtained therefrom by rearrangement was of poor quality and the yield fell by about 5%.

3. The procedure was as in Example 1, except that the excess pressure was lowered to 50 mm Hg and 4 $m^3$ of nitrogen were introduced per kg of cyclohexanone oxime. The cyclohexanone oxime evaporated was heavily discoloured as was the caprolactam obtained therefrom by rearrangement.

What we claim is:

1. A process for the evaporation of cyclohexanone oxime, which comprises evaporating the cyclohexanone oxime in the presence of an inert gas at a superatmospheric pressure of at least 300 Torr, the evaporation temperature being maintained in the range of from 110° to 160° C. by adjusting the inert gas pressure and/or by adjusting the ratio of cyclohexanone oxime to inert gas.

2. A process as claimed in claim 1, wherein the evaporation temperature is maintained in the range of from 120° to 140° C.

3. A process as claimed in claim 1, wherein the cyclohexanone oxime contains up to 10% by weight of water, based on the oxime.

* * * * *